United States Patent [19]
Bremmer et al.

[11] Patent Number: 5,977,412
[45] Date of Patent: Nov. 2, 1999

[54] PROCESS FOR PREPARING 3,5-DIFLUOROANILINE

[75] Inventors: Martin L. Bremmer, Rockford, Ill.; William J. Lipa, Chapel Hill, N.C.

[73] Assignee: BASF Corporation, Mount Olive, N.J.

[21] Appl. No.: 09/134,620

[22] Filed: Aug. 14, 1998

[51] Int. Cl.$^6$ .................................................. C07C 209/00
[52] U.S. Cl. ............................................ 564/405; 564/407
[58] Field of Search ...................................... 564/405, 407

[56] References Cited

U.S. PATENT DOCUMENTS

| | | |
|---|---|---|
| 5,157,169 | 10/1992 | Patton . |
| 5,204,366 | 4/1993 | Lavanish et al. . |
| 5,294,742 | 3/1994 | Schach et al. . |
| 5,399,767 | 3/1995 | Nasu et al. . |
| 5,498,794 | 3/1996 | Schach et al. . |
| 5,510,533 | 4/1996 | Kobayashi et al. . |

FOREIGN PATENT DOCUMENTS

PCT/FR95/00941 of 1995 WIPO .
WO9602493A1 2/1996 WIPO .

*Primary Examiner*—Paul J. Killos
*Attorney, Agent, or Firm*—Alston & Bird LLP

[57] ABSTRACT

The invention provides a novel process for producing a 3,5-difluoroaniline compound by reacting a 2-halo-4,6-difluoroaniline with a diazotizing agent in the presence of a reducing agent to form a diazonium salt. Build-up of potentially dangerous diazonium salt is avoided by reducing the diazonium salt with the reducing agent, to form a 1-halo-3,5-difluorobenzene, contemporaneously with the diazotization reaction. The 1-halo-3,5-difluorobenzene is then aminated.

27 Claims, No Drawings

5,977,412

PROCESS FOR PREPARING 3,5-DIFLUOROANILINE

FIELD OF THE INVENTION

The present invention relates to novel processes for the manufacture of 3,5-difluoroaniline compounds. More specifically, it relates to novel processes for the manufacture of 3,5-difluoroaniline compounds including halogenation of 2,4-difluoroaniline, and diazotization of halogenated 2,4-difluoroaniline to form a diazonium salt and contemporaneously reducing the diazonium salt, followed by amination.

BACKGROUND OF THE INVENTION 3,5-difluoroaniline is a known chemical with varied uses. It is particularly useful as an intermediate in production of herbicidal and pharmaceutical compositions. One known method for the production of 3,5-difluoroaniline is by amination of 1-bromo-3,5-difluorobenzene. Known processes for the manufacture of 1-halo-3,5-dihalobenzenes, including 1-bromo-3,5-difluorobenzene are discussed, for example, in U.S. Pat. No. 5,157,169, which issued to Patton on Mar. 26, 1992, the contents of which are incorporated herein by reference.

However, the processes discussed in the patent to Patton have several drawbacks. One particular drawback is the production in those processes of a diazonium salt as an intermediate. Diazonium salts can be explosive, and thus a build-up of diazonium salt in a manufacturing process presents an increased potential danger in carrying out such a process. According to the Patton reference, 2-bromo-4,6-difluoroaniline is diazotized in an aqueous solution of hydrochloric acid to afford a solution of diazonium salt. The diazonium salt is subsequently reduced using hypophosphorous acid. Thus, this process includes an increased level of danger particularly after the diazotization of 2-bromo-4,6-difluoroaniline and before reduction thereof with hypophosphorous acid. Moreover, the use of hypophosphorous acid is particularly costly.

Also, as set forth in the Patton reference, because the bromination reaction is exothermic, when conducted in an aprotic solvent, the reaction must be controlled to temperatures of less than 30° C. This necessitates cooling the reaction mixture with corresponding additional costs to the production process.

Another drawback to the process discussed in the Patton reference is the necessity of collecting and drying the 2-bromo-4,6-difluoroaniline hydrobromide salt after the bromination step and before diazotization. This step is time consuming, and thus, when the process is used on a commercial level, will result in significant additional costs in the production of a 1-bromo-3,5-difluorobenzene product. Moreover, producing 1-bromo-3,5-difluorobenzene in two distinct steps, separated by a drying step, requires additional equipment, at least inasmuch as two reaction vessels, as well as additional filtering and drying equipment, are required to practice the process.

Yet another disadvantage to that process is the yield. According the Patton reference, the process discussed therein results in a yield of 2-bromo-4,6-difluoroaniline of about 75% (mole basis).

In view of the significant commercial uses of 3,5-difluoroaniline, there has been substantial commercial research directed to identifying commercially acceptable, safe, inexpensive and efficient methods for manufacturing 3,5-difluoroaniline products in high yields. However, despite the commercial interest and substantial research to identify such processes, no process has been found in which high yields of 3,5-difluoroaniline are achieved by a generally safe, inexpensive process while minimizing separate steps to isolate intermediates.

SUMMARY OF THE INVENTION

In accord with the present invention a 2-halo-4,6-difluoroaniline compound is diazotized in the presence of a reducing agent, and the diazonium salts produced by that reaction are substantially simultaneously reduced to form a 1-halo-3,5-difluorobenzene, thus avoiding a potentially dangerous build-up of diazonium salts. Moreover, the diazotization reaction and concurrent reduction reaction according to the invention can be conducted within the same solution in which the 2-halo-4,6-difluoroaniline was previously produced by halogenation of a 2,4-difluoroaniline. The 1-halo-3,5-difluorobenzene is then separated and aminated to produce 3,5-difluoroaniline at a substantial yield, e.g., up to about 87% or higher in preferred embodiments of the invention. Thus, the present invention provides commercially acceptable methods for producing high yields of 3,5-difluoroaniline compounds, with improved safety, which methods can include separation of only one intermediate.

DESCRIPTION OF THE PREFERRED EMBODIMENTS

In the following detailed description, preferred embodiments of the invention are described to enable practice of the invention. It will be apparent that, although specific terms are used to describe and illustrate the preferred embodiments, these are used in the descriptive sense and not for the purpose of limiting the invention thereto. It will also be apparent that the invention is susceptible to numerous changes and may be embodied in many different forms other than the preferred embodiments specifically described below as will become apparent from a consideration of the invention described in the foregoing and hereafter.

The methods for producing 3,5-difluoroaniline of the present invention are based on the diazotization of a 2-halo-4,6-difluoroaniline compound in the presence of a reducing agent, so as to concurrently reduce the diazonium salt formed by the diazotization reaction while the diazotization reaction is continuing. In a preferred embodiment, reducing agents are $C_1$–$C_6$ alcohols. A particularly preferred reducing agent is isopropyl alcohol.

The 2-halo-4,6-difluoroaniline compound can be prepared according to the present invention by halogenation of 2,4-difluoroaniline with a halogenating agent, such as $Br_2$, in an aqueous acid solution, such as hydrochloric acid. In a preferred embodiment of the present invention, after the halogenation reaction, if there is a presence of excess halogenating agent, such excess is destroyed, resulting in an acid slurry of 2-halo-4,6-difluoroaniline. To the slurry, a large excess of $C_1$–$C_6$ alcohol reducing agent is added. The reducing agent also acts as a solvent for the diazotization reaction. A catalyst is also added to the slurry to aid in the reduction of the diazonium salt, and sodium nitrite is added as the diazotization agent. As the sodium nitrite is added, it reacts with the 2-halo-4,6-difluoroaniline to form the diazonium salt of the 2-halo-4,6-difluoroaniline. As the diazonium salt is formed, it is continually reduced, or decomposed, to form 1-halo-3,5-difluorobenzene, as well as nitrogen gas, acetone, sodium-halogen salt and water, with no significant accumulation of the diazonium salt intermediate.

The 1-halo-3,5-difluorobenzene is then isolated from the reaction mixture and is aminated by reaction with aqueous ammonia. Following amination, the 3,5-difluoroaniline is isolated from the reaction mixture.

In a preferred embodiment of the present invention, liquid 2,4-difluoroaniline is charged to a reaction vessel containing aqueous hydrochloric acid to form the hydrochloride salt of 2,4-difluoroaniline. Much of the salt is soluble in the aqueous solution, and the remainder forms a fluid, easily agitated slurry. In a preferred embodiment, the amount of hydrochloric acid is about 2.5 equivalents of hydrochloric acid per equivalent of 2,4-difluoroaniline to be reacted. However, the amount of hydrochloric acid can be increased, for example, up to 4 equivalents of hydrochloric acid per equivalent of 2,4-difluoroaniline to be reacted, without detrimental effects. In a preferred embodiment, sufficient water is added to dilute the initial hydrochloric acid charge to about 12.5% by weight of the initial solution.

The salt is then brominated directly to 2-bromo-4,6-difluoroaniline by the addition of one equivalent of elemental bromine. It has been found that this bromination reaction can be completed successfully at temperatures reaching 45° C., thus requiring little or no cooling of the reaction vessel when the bromine is added gradually, for example, over 50 minutes when reacting about 100 pounds of 2,4-difluoroaniline. The addition of elemental bromine to the slurry also results in generation of hydrogen bromide, and accordingly in addition to the hydrochloride salt of 2-bromo-4,6-difluoroaniline, the hydrobromide salt of 2-bromo-4,6-difluoroaniline is generated, the presence of which has been found to be beneficial in producing high yields in the subsequent diazotization reaction.

Following bromination, the slurry resulting from the bromination reaction might have small amounts of excess bromine. In such an event, excess bromine can be reduced and removed by treating the slurry with a small amount of sodium sulfite. After reducing any excess bromine, the 2-bromo-4,6-difluoroaniline hydrochloride or hydrobromide is diazotized by first adding an excess of isopropyl alcohol or other $C_1$–$C_6$ alcohol, a catalytic amount of cuprous oxide or other cuprous salt, and then a slight molar excess of sodium nitrite.

One molar equivalent of alcohol, based on the 2-bromo-4,6-difluoroaniline being reacted, is consumed in the reduction of the diazonium salt. However, in a preferred embodiment about six molar equivalents, based on the initial 2,4-difluoroaniline charge, are used to provide acceptable reaction performance. In a particular preferred embodiment, about 9.3 molar equivalents of isopropyl alcohol are used, so as to ameliorate subsequent isolation of the 1-bromo-3,5-difluorobenzene by distillation.

The addition of the cuprous oxide catalyst, or other cuprous salt, serves to accelerate the rate of reduction of the diazonium salt so that diazonium salt accumulation does not occur. In a preferred embodiment, between about 2 mole percent and about 20 mole percent of cuprous oxide, based on the initial 2,4-difluoroaniline charge, is added. In a particular preferred embodiment, about 6 mole percent of cuprous oxide, based on the initial 2,4-difluoroaniline charge, is added.

The sodium nitrite is added preferably as a free-flowing, white, crystalline solid, but can also be added as a preformed aqueous solution. The sodium nitrite is added gradually, with good agitation, so as to control the formation of the diazonium salt. In a preferred embodiment, an amount of sodium nitrite is added that is about a 1 to about a 2 molar percent excess based on the initial 2,4-difluoroaniline charge. The sodium nitrite is added over a period of about 1.5 to about 2.0 hours, while maintaining the reaction temperature at less than about −10° C. In a preferred embodiment the sodium nitrite is added at a rate such that a smooth evolution of nitrogen gas from the reaction is maintained until the reaction is complete. As the diazonium salt is formed, the isopropyl alcohol and cuprous oxide catalyst continually reduce the diazonium salt, converting it to 1-bromo-3,5-difluorobenzene, thus avoiding accumulation of the diazonium salt and alleviating safety concerns related thereto.

After the diazotization and reduction reactions have been completed, the reaction mixture is neutralized to a pH from about 3 to about 4. The 1-bromo-3,5-difluorobenzene is distilled from the reaction mixture as a component of a 1-bromo-3,5-difluorobenzene/isopropyl alcohol/water azeotrope. After distillation, the distillate is added to an amount of water weighing about twice the weight of the distillate. This results in the separation of 1-bromo-3,5-difluorobenzene as a dense, second phase. The yield of 3,5-difluorobenzene from 2-bromo-4,6-difluoroaniline according to this process can be about 92%. If the 1-bromo-3,5-difluorobenzene has more than about 0.5% to 1.0% residual acetone, the acetone is preferably removed by water wash of the 1-bromo-3,5-difluorobenzene.

The upper phase of the separation can be distilled to recover isopropyl alcohol which can be recycled. A small initial forecut of the distillate contains the bulk of acetone remaining in the solution and can be discarded. Following the forecut, a small midcut is taken which contains isopropyl alcohol, the remainder of the acetone, and a small amount of 1-bromo-3,5-difluorobenzene. To recover the 1-bromo-3,5-difluorobenzene, the midcut can be recycled back to a subsequent 1-bromo-3,5-difluorobenzene phase separation. Following the midcut, the bulk of the isopropyl alcohol is distilled out as the isopropyl alcohol/water azeotrope and can be recycled back to the diazotization reaction.

Following separation of the 1-bromo-3,5-difluorobenzene, the 1-bromo-3,5-difluorobenzene is then aminated with an excess of aqueous ammonia under pressure in the presence of catalytic amounts of cuprous oxide. In a preferred embodiment, six molar equivalents of aqueous ammonia, in a 29% aqueous solution, is used. In a preferred embodiment, about 0.02 to about 0.04 molar equivalents of cuprous oxide, based on amount of 1-bromo-3,5-difluorobenzene to be reacted, are used to catalyze the amination reaction. In a preferred embodiment, reaction pressure is controlled at about 300 psig or less by maintaining the temperature of the reaction mixture at an initial temperature of about 135° C., and slowly increasing the temperature to 165° C. over a period of about 4.5 hours. The temperature is then maintained at about 165° C. for about one hour after reaching that temperature. 3,5-difluoroaniline is produced at a yield of about 95%, and one equivalent of ammonium bromide, as well as other byproducts, are also produced. The 3,5-difluoroaniline is isolated via extraction with an organic solvent such as, for example, methyl-tert-butyl ether. In a preferred embodiment, 0.55 lbs. of methyl-tert-butyl ether is used per pound of reaction mixture. The aqueous ammonia/ammonia bromide phase can then be neutralized with 50% sodium hydroxide. Overall, the 2,4-difluoroaniline can be converted to 3,5-difluoroaniline according to the inventive process in a yield of about 87%.

The following examples are intended to illustrate desirable methods provided according to the invention. However, as will be apparent, they are not intended as limitations thereon.

EXAMPLES

Preparation of 100 lbs. of 3.5-difluoroaniline

1. Bromination

In the preparation of 100 lbs. of 3,5-difluoroaniline, the initial bromination of 2,4-difluoroaniline to 2-bromo-4,6-difluoroaniline can be carried out as follows:

First a suitable glass-lined reactor is charged with 484.7 lbs. of water, and then with 257.8 lbs. of 32% hydrochloric acid. While maintaining the temperature at less than 30° C., 116.8 lbs. of 2,4-difluoroaniline is added to the hydrochloric acid solution to form a slurry of 2,4-difluoroaniline hydrochloride. The slurry is cooled to 20° C., and then 145.9 lbs. of bromine is added over a 50 minute period, thus maintaining the temperature at less than 45° C. The temperature is held between 20° C. and 45° C. for 30 minutes.

The reaction slurry is assayed, and is considered complete when residual 2,4-difluoroaniline is less than 0.5% of the initial charge (i.e., 99.5% conversion to 2-bromo-4,6-difluoroaniline). If it is necessary to react unreacted 2,4-difluoroaniline, an equivalent of bromine is added for each equivalent of unreacted 2,4-difluoroaniline, and the reaction is continued for an additional 30 minutes. When the reaction is complete, a reaction sample is assayed for free bromine, and an equivalent of solid, crystalline sodium sulfite is added for each equivalent of free bromine. Generally, about 1.0 pound of sodium sulfite is sufficient, and the solution is allowed to react at ambient temperature for 30 minutes.

2. Diazotization and Reduction

The conversion of the 2-bromo-4,6-difluoroaniline generated in the bromination reaction described above to 1-bromo-3,5-difluorobenzene can be carried out as follows:

The 2-bromo-4,6-difluoroaniline hydrochloride slurry, weighing about 1005 lbs., is contained in a glass-lined reactor suitable for cooling to a minimum of −10° C. To the slurry, 505 lbs. of isopropyl alcohol is added, and 7.76 pounds of cuprous oxide is added. The mixture is agitated and cooled to −10° C. to −15° C. Over a period of 1.5 to 2.0 hours, 63.5 lbs. of solid sodium nitrite is added while agitating the mixture and maintaining the temperature below −10° C. Steady evolution of nitrogen gas begins shortly after addition of the sodium nitrite begins, and indicates that the reaction is progressing.

The reaction mixture is held and agitated, maintaining the temperature at below −10° C., for 1.0 hour after sodium nitrite addition is complete. The reaction mixture is then assayed for unreacted 2-bromo-4,6-difluoroaniline. If unreacted 2-bromo-4,6-difluoroaniline is less than 0.2 molar percent relative to 1-bromo-3,5-difluorobenzene, the reaction is considered complete. Typically no unreacted aniline is detected. The reaction mixture is also assayed for undecomposed diazonium salt. A properly calibrated nitrogen flow meter on the reactor is also helpful in this respect to determine the termination of nitrogen evolution. If significant residual diazonium salt is detected, the reaction mixture is agitated for an additional 30 minutes, at a temperature below −10° C., and then re-checked until no significant residual diazonium salt is detected.

The reaction mixture is then warmed to ambient temperature over a 1 hour period. Using cooling water to maintain the temperature below 50° C., the reaction mixture is neutralized to a pH of 3 to 4 by the addition of about 171.5 pounds of 50% sodium hydroxide. The final reaction mixture is a two-phase system consisting of a dark purple top phase comprising isopropyl alcohol and 1-bromo-3,5-difluorobenzene, and a bottom aqueous brine phase.

The reaction mixture is charged to a suitable distillation unit, having 3–4 theoretical stages and equipped for reflux control. The distillation charge is brought to reflux, and the 1-bromo-3,5-difluorobenzene/isopropyl alcohol/water azeotrope is distilled out at an overhead temperature of about 56° C. to about 83° C. and pot temperature of about 79° C. to about 109° C. Acceptable results are obtained with reflux ratios of from about 3:1 to about 1:1. A total of about 760.4 lbs. of azeotrope product is collected overhead, containing about 450.6 lbs. of isopropyl alcohol, 52.6 lbs. of acetone, 95.0 lbs. of water, 160.6 lbs. of 1-bromo-3,5-difluorobenzene, and 1.5 lbs. of other organics, primarily difluorobenzene. An aqueous brine bottom stream of about 965 lbs. remains for treatment and waste disposal.

The 1-bromo-3,5-difluorobenzene azeotrope is transferred to a suitable agitated vessel equipped for phase separation. 1520 lbs. of water is added and mixed to the azeotrope to phase out the 1-bromo-3,5-difluorobenzene product. Agitation is stopped, and the phases are allowed to separate for 1.0 hour. 168.2 lbs. of 1-bromo-3,5-difluorobenzene product phase is separated as the bottom phase, containing 158.2 lbs. of 1-bromo-3,5-difluorobenzene, 5.9 lbs. of isopropyl alcohol, 1.5 lbs. of acetone, 1.4 lbs. of difluorobenzene, 0.7 lbs. of other organics, and 0.5 lbs. of water. If the acetone is determined to be greater than 1.0% of the solution, then the solution is further washed with water. This 1-bromo-3,5-difluorobenzene solution is then aminated to produce 3,5-difluoroaniline.

3. Amination

The 1-bromo-3,5-difluorobenzene generated by diazotization of 2-bromo-4,6-difluoroaniline can be converted to 100 lbs. of 3,5-difluoroaniline as follows:

A suitable pressure reactor designed for a minimum of 300 psig pressure is charged with 288.1 lbs. of 29% aqueous ammonia. The reactor is designed to provide for pressure control via temperature control of the reaction. To the ammonia charge, 4.7 lbs. of cuprous oxide is added, and the 168.2 lbs. of crude 1-bromo-3,5-difluorobenzene product is added. The reaction mixture is heated to about 135° C. using temperature control to maintain a maximum pressure of 300 psig, and the reaction pressure is maintained at about 300 psig by slowly increasing the reaction temperature to 165° C. over 4.5 hours.

The reaction mixture is held at 165° C. for one additional hour, and then a sample is assayed for completeness of the reaction. If more than 0.5% by weight of 1-bromo-3,5-difluorobenzene remains unreacted, then the reaction mixture is held at 165° C. for one more hour and re-assayed. This process is repeated until less than 0.5% by weight of unreacted 1-bromo-3,5-difluorobenzene remains.

The reaction mixture is cooled to ambient temperature, and 66.9 lbs. of 50% sodium hydroxide is added, and the mixture is agitated for 30 minutes, to neutralize the dissolved ammonium bromide byproduct, and thus raise the pH of the mixture to about 12. Following neutralization, 253.6 lbs. of methyl-tert-butyl ether is added, and the mixture is agitated for 30 minutes to extract the 3,5-difluoroaniline. Agitation is stopped, and the phases are allowed to separate for one hour. The 1-bromo-3,5-difluorobenzene/methyl-tert-butyl ether phase is separated and contains 100 lbs. of 3,5-difluoroaniline, as well as about 1.2 lbs. of 3-fluoroaniline, about 1.5 to 2.0 lbs. of 1,3-difluorobenzene, and possibly lesser amounts of other reaction by-products.

The invention has been described in considerable detail with reference to its preferred embodiments. However, numerous variations and modifications can be made without departure from the spirit and scope of the invention as described in the foregoing detailed specification and defined in the appended claims.

That which is claimed is:

1. A process for producing a 3,5-difluoroaniline compound comprising reacting a 2-halo-4,6-difluoroaniline with a diazotizing agent in the presence of a reducing agent to form a diazonium salt, and substantially concurrently with said diazotization reaction reducing said diazonium salt so as to form a 1-halo-3,5-difluorobenzene, and aminating said 1-halo-3,5-difluorobenzene.

2. The process according to claim 1, wherein said reducing agent is a $C_1$–$C_6$ alcohol.

3. The process according to claim 2, wherein said reducing agent is isopropyl alcohol.

4. The process according to claim 1, wherein said diazotizing agent is sodium nitrite.

5. The process according to claim 2 further comprising reducing said diazonium salt in the presence of a catalyst.

6. The process according to claim 5 wherein said catalyst is a cuprous salt.

7. The process according to claim 5 wherein said catalyst is cuprous oxide.

8. The process according to claim 2 further comprising providing said 2-halo-4,6-difluoroaniline by halogenating a 2,4-difluoroaniline compound with a halogenating compound in the presence of a solvent.

9. The process according to claim 8 wherein said solvent is aqueous hydrochloric acid.

10. The process according to claim 9 wherein the halogenating compound is represented by the formula $X_2$, wherein X is a halogen.

11. The process according to claim 10 wherein X is bromine.

12. The process according to claim 8 wherein said step of reacting a 2-halo-4,6-difluoroaniline with a diazotizing agent is performed in the presence of said solvent of said halogenating step.

13. The process according to claim 8 further comprising reacting an excess of said halogenating compound with a halogenating compound reducing agent.

14. The process according to claim 13 wherein said halogenating compound reducing agent is sodium sulfite.

15. The process according to claim 9 wherein said hydrochloric acid is present in said halogenating step in an amount between about 2.5 equivalents and about 4.0 equivalents of hydrochloric acid per equivalent of 2,4-difluoroaniline.

16. The process according to claim 9 wherein said hydrochloric acid is present in said halogenating step in an amount about 2.5 equivalents of hydrochloric acid per equivalent of 2,4-difluoroaniline.

17. The process according to claim 2 wherein said $C_1$–$C_6$ alcohol is present in an amount of from about 1.0 equivalents to about 10.0 equivalents of $C_1$–$C_6$ alcohol per equivalent of 2-halo-4,6-difluoroaniline being reacted.

18. A process for producing a 3,5-difluoroaniline compound comprising halogenating a 2,4-difluoroaniline compound with a halogenating compound in the presence of a solvent to form a 2-halo-4,6-difluoroaniline, reacting said 2-halo-4,6-difluoroaniline with a diazotizing agent in the presence of said solvent and a reducing agent to form a diazonium salt, and substantially concurrently with said diazotization reaction reducing said diazonium salt so as to form a 1-halo-3,5-difluorobenzene, and aminating said 1-halo-3,5-difluorobenzene.

19. The process according to claim 18, wherein said reducing agent is a $C_1$–$C_6$ alcohol.

20. The process according to claim 19, wherein said reducing agent is isopropyl alcohol.

21. The process according to claim 19, wherein said solvent is aqueous hydrochloric acid.

22. The process according to claim 21, wherein the halogenating compound is represented by the formula $X_2$, wherein X is a halogen.

23. The process according to claim 22, wherein X is bromine.

24. The process according to claim 23, further comprising reacting said 2-halo-4,6-difluoroaniline with said diazotizing agent in the presence of a catalyst.

25. The process according to claim 24, wherein said catalyst is a cuprous salt.

26. The process according to claim 24, wherein said catalyst is cuprous oxide.

27. The process according to claim 19, wherein said diazotizing agent is sodium nitrite.

* * * * *